United States Patent [19]

Reiner

[11] Patent Number: 4,939,291

[45] Date of Patent: Jul. 3, 1990

[54] PROCESS FOR THE PREPARATION OF MERCAPTOETHANSULFONIC ACID AND SODIUM SALT THEREOF

[75] Inventor: Alberto Reiner, Cantù, Italy

[73] Assignee: Schering Spa, Milan, Italy

[21] Appl. No.: 346,320

[22] Filed: May 1, 1989

Related U.S. Application Data

[63] Continuation of Ser. No. 102,668, Sep. 30, 1987.

[30] Foreign Application Priority Data

Oct. 8, 1986 [IT] Italy ............................. 21934 A/86

[51] Int. Cl.$^5$ ............................................. C07C 143/02
[52] U.S. Cl. .................................... 562/108; 558/252; 564/183
[58] Field of Search ................ 562/211, 108; 558/252; 564/183

[56] References Cited

U.S. PATENT DOCUMENTS 2,694,723  11/1954  Schramm ..................... 260/501.21

FOREIGN PATENT DOCUMENTS 842665    12/1976  Belgium .
0198542   10/1986  European Pat. Off. .
198542    10/1986  European Pat. Off. .
1056602    5/1959  Fed. Rep. of Germany .

OTHER PUBLICATIONS

Chemical Abstracts, vol. 50, No. 4, Feb. 25, 1956, p. 1956, col. 2422d, VXIII.

*Primary Examiner*—Bruce Gray
*Attorney, Agent, or Firm*—Armstrong, Nikaido Marmelstein, Kubovcik & Murray

[57] ABSTRACT

For the preparation of saline derivatives of mercaptoethansulfonic acid belonging to the class of the salts of alkali metals and of the salts with basic aminoacids, the sodium salt of the acid is obtained with a process comprising the reaction between sodium bromoethansulfonate with thiobenzoic acid and sodium bicarbonate and subsequent reaction of the resulting sodium benzoylethansulfonate with ammonia in water solution.

4 Claims, No Drawings

PROCESS FOR THE PREPARATION OF MERCAPTOETHANSULFONIC ACID AND SODIUM SALT THEREOF

This application is a continuation of application Ser. No. 102,668 filed Sept. 30, 1987.

The present invention relates to process for the preparation of saline derivatives of mercaptoethansulfonic acid having general formula:

$$HS-(CH_2)_2-SO_3^{\ominus} \overset{R}{\underset{H}{\overset{|}{N}}}{\overset{\oplus}{\phantom{N}}}\!\!\!\!{-Z}\quad\quad (I)$$

wherein R represents H,

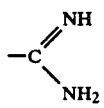

and Z represents an alkali metal or the radical of a basic aminoacid or of alkyl ester thereof.

The mercaptoethansulfonic acid is known from the therapeutical point of view as a mucolytic drug for the respiratory tract. However the administration can only take place by aerosol route. Owing to the remarkable instability of this chemical compound it can not be taken into consideration in free state, but only in form of a salt or other derivatives, such as for instance the sodium salt. Just in this form it has been foreseen and used either as mucolytic for the upper respiratory tract, and as antidote in the case of haemorrhagic cystitis induced by anti-tumoral drugs (German Laid Open Application No. 2756018 of Dec. 14, 1977, in the name of ASTA WERKE A. G.).

Recent research studies have moreover disclosed the marked activity of mercaptoethansulfonic acid and of the derivatives thereof capable of releasing it into the organism, as an anti-tumoral drug in the treatment of the bladder carcinoma as well as in the treatment and in the prevention of cistinic kidney calculi (European Patent Application No. 86.200.597.2).

It is thus evident that the importance at the present time of preparing those derivatives in an industrially advantageous manner and in form of suitable purity for the therapeutical use. The main purpose of the present invention is therefore that of providing a process for the preparation of the derivatives of mercaptoethansulfonic acid having formula (I).

Such a purpose is achieved by a process which is characterized by the following steps:
(a) reaction between sodium bromoethansulfonate and thiobenzoic acid added with sodium bicarbonate at a temperature of 85°–90° C. and in aqueous solvent leading to sodium benzoyl thiothansulfonate;
(b) reaction of sodium benzoyl-thiothanesulfonate with ammonia in aqueous solution under nitrogen flow and at a temperature of about 50° C. under stirring with precipitation of benzamide and the obtention of sodium mercaptoethansulfonate.

The salts of amino acids and alkyl esters of amino acids encompassed by the formula (I) are prepared by a process which comprises the steps of releasing the mercaptoethansulfonic acid from its sodium salt and reacting the obtained mercaptoethansulfonic acid with the desired basic aminoacid. The free mercaptoethansulfonic acid may be released from its sodium salt through the use of a strong cationic resin, for example AMBERLITE I.R. 20, taking care to operate under a nitrogen stream and at a temperature in the range of 5°–10° C. in order to prevent thiolic bonds from being formed. The just-released mercaptoethansulfonic acid is reacted with an equimolar amount of the desired basic amino acid in an aqueous or hydroalcoholic medium. In turn the sodium bromoethanesulfonate can be prepared from dibromethane and sodium sulfite refluxed using as the solvent ethanol and water.

The process of the present invention is clearly illustrated from the following scheme:

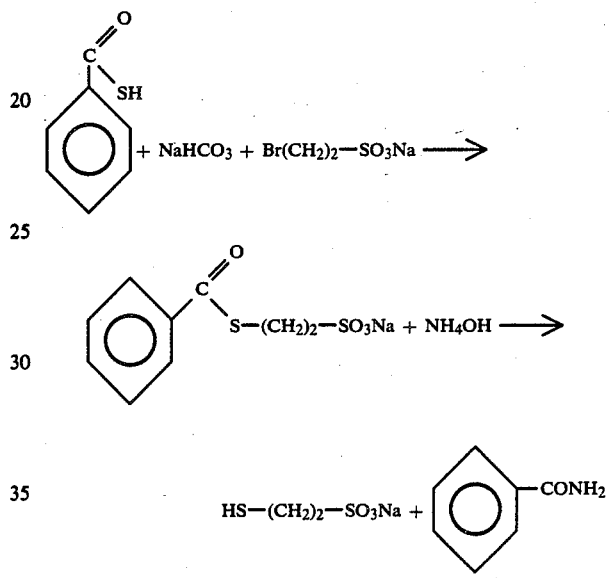

There is now described an embodiment of the process of the present invention, it being meant that is has only illustrative but in no way limiting purpose.

(1) Preparation of sodium bromoethansulfonate

In a 10 l flask, provided with refluxing serpentine, mechanical stirrer, termometer and separating funnel, there are charged in the order in the following amounts of reactants:

| | |
|---|---|
| 3050 ml of 95% ethanol (techinal grade) | mixture (A) |
| 1500 ml of dibromoethane | |
| 1100 ml of distilled water | |

This mixture is heated to the refluxing temperature of the liquid phase.

Separately the following solution is prepared:

| | |
|---|---|
| 305.5 g of sodium sulfite | mixture (B) |
| 1100 ml of deionized water | |

This solution (mixture B) is charged in the separating funnel mounted to the reacting flask and is slowly added into the flask already containing the liquid (mixture A) undergoing reflux. The reaction mixture is distilled with vapor passing at a temperature of 78° C. and which are represented by a mixture of excess dibromoethane and of ethyl alcohol.

The distillation is stopped when in the flask a solution remains, amounting to about 1800 ml and containing the product, sodium bromoethansulfonate, with the inorganic salts, sodium bromide and unreacted sodium sulfite.

The solution is concentrated to dryness under vacuum by reducing the volume to about 600 ml and this volume is formed from organic and inorganic salts.

This crystalline phase of the mixture is taken up with 6 liters of 94% ethanol and the mixture is heated under stirring to reflux for 1 hour. The mixture is separated by hot filtration from the undissolved salt (105 g on dry basis) and ethanolic waters, cooled down to 15° C. for 3 hours, give place to a white precipitate of pearly aspect having the weight of 330 g (on dry basis) which, as such, is used for the next phase. The foreseen consumption of dibromethane, for 300 g of sodium bromoethane sulfonate, is about 300 g.

The alcoholic solution distilled together the dibromethane is totally recovered and used in the subsequent reaction with a proportional addition of the needed bisulfite which is left in identical amount with respect to the first reaction and there are obtained further 290 g of sodium dibromoethanesulfonate.

Then a further reaction is carried out with lower amounts of sodium sulfite.

Reaction yield: 330 g of sodium bromoethansulfonate.

(2) Preparation of sodium benzoylthioethansulfonate

Into a 1000 ml flask, provided with refluxing device, stirrer and thermometer, the following amounts are charged in the order:

| water 350 ml | |
|---|---|
| sodium bromoethansulfonate 100 g | mixture (1) |

Separately the following compounds are charged in a beaker:

| water 350 ml | |
|---|---|
| thiobenzoic acid 69 g | mixture (2) |

42 g of sodium bicarbonate are added in portions to the mixture (2). At that point the solution obtained of the mixture (2) is filtered to remove all the impurities contained in the thiobenzoic acid. To the flask containing the mixture (1) the mixture (2) is added all at once under stirring and the resulting mixture is heated under stirring at a temperature of 85°-90° C. for 16 hours.

There is obtained a solution of slightly yellow pink colour which at the end of the 16 hours period is about 800 ml on the whole and is directly concentrated to 300 ml with precipitation of a pink product as pearly crystals of sodium benzoylthio ethansulfonate. The solution, after cooling to 20° C., is filtered under vacuum and a crystalline pink product is obtained having a wet weight of 95 g. It is taken as such with acetone in the ratio 1:5 weight/volume, is filtered and dried under vacuum at 60° C. leading to 77 g of chromatographically pure crystalline product with a yield of 60% of the theoretical value.

(3) Preparation of sodium mercaptoethansulfonate

Into a flask provided with stirrer, refrigerator, continuous flow of nitrogen, thermometer, the following amounts are charged in the order:
deionized water 420 ml
sodium benzoylthioethansulfonate 70 g
ammonia as a 25% solution in water 53.3 g The reaction mixture is brought to an internal temperature of 50° C. under stirring and under nitrogen stream and it is maintained to such a temperature for 3.30 hours on the whole. During the reaction an abundant precipitate of white product is obtained corresponding to benzamide.

At the end of the reaction the mixture is cooled down to 5° C., filtered from benzamide and the aqueous solution is concentrated to ⅓ of the volume.

It is filtered from the further amount of benzamide and then the aqueous solution containing the sodium thioethansulfonate is concentrated to dryness. The theoretical yield of active principle of 42.6 g and in the flask it remains with water to a total weight of 67 g. There are added also 600 ml of methanol (1:15 with respect to the theoretical), is heated to 40° C. under stirring and at such a temperature it is filtered and the product remains in solution; it is collected by cooling and filtering, leading to 21 g on dry basis (35 g on wet basis) which are poured in the ratio of 1:2 in absolute ethanol at 50° C. and are filtered giving 21 g on dry basis.

From the concentration of the methanolic waters to ⅓ of the volume 20 g are obtained (on wet basis), which, after treatment with ethanol, give place to 11 g on dry basis. All the washing ethanolic waters upon being dried give, place to further 4 g of a product which is found good at the analysis whereby a total of 36 g is obtained (in comparison with theoretical yield of 42.6 g.).

I claim:
1. A process for the preparation of sodium mercaptoethansulfonate comprising the steps of:
    (a) reacting sodium bromoethansulfonate with thiobenzoic acid in the presence of sodium bicarbonate at a temperature of 85°-90° C. in an aqueous solvent consisting essentially of water, to give sodium benzoyl thioethansulfonate; and
    (b) reacting the obtained sodium benzoyl thioethansulfonate with ammonia in aqueous solution under nitrogen flow and at a temperature of about 50° C. with stirring to precipitate benzamide and give sodium mercaptoethansulfonate.

2. A process as in claim 1, wherein the sodium bromoethansulfonate is prepared by reacting dibromoethane and sodium sulfite in a solvent mixture consisting essentially of ethanol and water at a temperature sufficiently high to cause refluxing of the liquid phase of the reaction mixture.

3. A process for the preparation of mercaptoethansulfonic acid comprising the steps of:
    (a) reacting sodium bromoethansulfonate with thiobenzoic acid in the presence of sodium bicarbonate at a temperature of 85°-90° C. in an aqueous solvent consisting essentially of water, to give sodium benzoyl thioethansulfonate;
    (b) reacting the obtained sodium benzoyl thioethanesulfonate with ammonia in aqueous solution under nitrogen flow and at a temperature of about 50° C.

with stirring to precipitate benzamide and give sodium mercaptoethansulfonate; and
(c) releasing mercaptoethansulfonic acid from the obtained sodium mercaptoethansulfonate by use of a strong cationic resin under a nitrogen stream and at a temperature in the range of 5°–10° C.
4. A process as in claim 3, wherein the sodium bromoethansulfonate is prepared by reacting dibromoethane and sodium sulfite in a solvent mixture consisting essentially of ethanol and water at a temperature sufficiently high to cause refluxing of the liquid phase of the reaction mixture.

* * * * *